US007795502B2

(12) United States Patent
Barta et al.

(10) Patent No.: US 7,795,502 B2
(45) Date of Patent: Sep. 14, 2010

(54) ATRSP GENE PROMOTERS

(75) Inventors: Andrea Barta, Rannersdorf/Schwechat (AT); Sergiy Lopato, Plympton (AT); Maria Kalyna, Vienna (AT)

(73) Assignee: Syngenta Participations AG, Basel (CH)

( * ) Notice: Subject to any disclaimer, the term of this patent is extended or adjusted under 35 U.S.C. 154(b) by 552 days.

(21) Appl. No.: 11/805,975

(22) Filed: May 25, 2007

(65) Prior Publication Data

US 2008/0256670 A1 Oct. 16, 2008

Related U.S. Application Data

(62) Division of application No. 10/240,496, filed as application No. PCT/EP01/03735 on Apr. 2, 2001, now Pat. No. 7,256,276.

(30) Foreign Application Priority Data

Apr. 3, 2000 (GB) .................. 0008120.8

(51) Int. Cl.
*A01H 5/00* (2006.01)
*C12N 15/82* (2006.01)

(52) U.S. Cl. .................. 800/295; 800/312; 800/320; 435/468

(58) Field of Classification Search ........................ None
See application file for complete search history.

(56) References Cited

FOREIGN PATENT DOCUMENTS

WO    WO 98/44781    10/1998

OTHER PUBLICATIONS

Nakamura (EMBL database, Sequence accession No. AB015478.1; Published in DNA Res. 5:297-308, 1998).*
Moloney et al. (Plant Cell Reports, 8:238-242, 1989).*
Kasuga et al. (Nature Biotechnology, 17:287-291, Published Mar. 1, 1999).*
Lopato et al., The Plant Cell, vol. 8 (Dec. 1996), pp. 2255-2264.
Nakamura et al., Arginine/serine-rich splicing factor RSP41 homolog, Database EMPLN (online), pp. 1-3, Jun. 19, 1998.
Nakamura et al., DNA Research, vol. 5, pp. 297-308, 1998.
File History of U.S. Patent No. 7,256,276.

* cited by examiner

*Primary Examiner*—Vinod Kumar
(74) *Attorney, Agent, or Firm*—Bruce Vrana

(57) ABSTRACT

This invention describes novel DNA sequences that function as promoters of transcription of associated nucleotide sequences. More specifically, this invention describes DNA sequences conferring constitutive expression to an associated nucleotide sequence. The invention also describes recombinant sequences containing such promoter sequences. The said recombinant DNA sequences may be used to create transgenic plants, but especially transgenic plants expressing a nucleotide sequence of interest at all times and in most tissues and organs.

4 Claims, No Drawings

SEQUENCE LISTING

<160> NUMBER OF SEQ ID NOS: 8

<210> SEQ ID NO 1
<211> LENGTH: 2327
<212> TYPE: DNA
<213> ORGANISM: Arabidopsis thaliana

<400> SEQUENCE: 1

```
ttgaattagc attgtgttgt gtaacaaatt gcagagcttg gtgttgatgt tgcagagctg      60
ggattatgta cacttcaagt gttggaggag aggttgacca aaacttaaaa tccggagagt     120
tgtcgttgac cgggactggc tttctcggtg ctgttggccg gagtttagac ttgggtatat     180
aaactaatca aagcttttta tttaccattg ctcgcttttg tacttcaacg ttgatgaatg     240
tgtgtgtttg ggatgatcat aggagggcaa actgcgttgg cattgcgact tctattggcg     300
gttttctctt ctaagttatc ttctgttgct gaccgccctt tcggggatga ggtacttttg     360
agaaaacctc aagagttagt gtttgtcttt ggacattcag tctcttcttg attgctattt     420
gttgcagttt cgtgctgctc ggaaagcatc tgaggaagtt ggtgcgcagc tggttcttgg     480
agatcgaccc atcgaaataa ctgtaatgac tataccaagt accaactgat cgttttgta      540 gttacatatg ggtttaaaac caatggaatc tacattgaac ttataacatt gtagctccaa     600
agggcttgga actctttgaa atggggagag aagtttaatc tggtgatggc tgtgactcgg     660
gtaatcacat cgtcatcggg tatatccgca gcggagctta aggttttgtt tctctttcgc     720
taactcggtt tcgctttaat tcaagaagat gataagataa gttgtaactt ttcggtttgt     780
gtttgcattg caacaggaac aagagaccga tgaaaacagt ggaagtttgc agctttacga     840
acggctaagt ttctcatacc cggcactcct aatgcctctt atacacgaaa gagataccgt     900
aagcataaaa accgaaacaa agcgacactc aaaaaaaccg tatgctgata agacttgacc     960
aaataatgtg ttttttttgcc ttgacagtat cttgcttggt cattgaagag aagtaaggca    1020
gtgaatgggt gtaaaacagt ggtgggagtg atcgggaaag gacacatgaa tggtgtcatc    1080
tacgcgttgg tgtcagactc tggggatctc cggtttagag atttggtggg aagaggagat    1140
tcatataatg gtggtactgg tactacatcg aacggttgga ttcaaaaggt tttaaagagc    1200
ttcgtaagag acacaattat agggttcttg ctatgggagt tatatgaaca gtatctgatg    1260
atgaatcaaa acctttcatg atataactaa aaaaacaagt tgttgcatat ttaaaaagga    1320
aactggaaaa agaatctaaa tgagtacaat atgtatgtat atgattcttc ttcctctaga    1380
ttttgttgag gcaactacaa agtcttatat gaaattgatg tatattttgc agaaatttca    1440
attgtaaaca taaaatgttt aggtaaaaaa ttatttgtac ttctctagtt ggtaacgaaa    1500
```

```
taaaaataaa atatttttt ttttaatata tatatatata tatatataaa tataaatata    1560
tgtttaagat tcattatctg gagagagagc ctcgaagaaa gcaaataaaa tctagagaag    1620
cttgtttcta gggtttcgac tctcgacggc cggtacgatt tttcaactgc ttgttctaag    1680
gtataatcaa aatcgagttc ttcagatatt gaattcgatt ctctctttgg tctctctctt    1740
ctcttgttct tcagatttaa attcgatagc ttttttcattt tcttccgttg aattttttctt   1800 gtttcattag gtctgttgaa attgtagttt cttcttgctt tgttttctca tatggttgat    1860 ttttttttc cagatctgag gttttttttca tcatagcttg aaaaaatcca tactttctgg    1920
gcttcctttg tataaatatg aaaactttaa tgaaaatctg ttgtggtatg ttatgggttg    1980
tgacttgtga tgaattgaat tttgaatata gttgtaaatt tgaaatcttg aagtatgaaa    2040
tttgcattgg tttgttaatt tgtgatgaat tggattttga ttattacagt tataaagttg    2100
aaaacttgga agtgtagatg attacatttt tctgtggttt ggttcctgtt atgttcattg    2160
ttctatgatc ttaattatat gttttgttat tgcttctctt ctggagtgtg tttatttgta    2220
tattttggtc aaatctgtgc tctgtttagt atctcttgga tatcttttga tacttaggtt    2280
gttgagagga gctataaatc gtttctgttg tctattttgt aggaatc                 2327

<210> SEQ ID NO 2
<211> LENGTH: 2137
<212> TYPE: DNA
<213> ORGANISM: Arabidopsis thaliana

<400> SEQUENCE: 2
aagcttttta tttaccattg ctcgcttttg tacttcaacg ttgatgaatg tgtgtgtttg      60
ggatgatcat aggagggcaa actgcgttgg cattgcgact tctattggcg gttttctctt     120
ctaagttatc ttctgttgct gaccgccctt tcggggatga ggtacttttg agaaaacctc     180
aagagttagt gtttgtcttt ggacattcag tctcttcttg attgctattt gttgcagttt     240
cgtgctgctc ggaaagcatc tgaggaagtt ggtgcgcagc tggttcttgg agatcgaccc     300
atcgaaataa ctgtaatgac tataccaagt accaactgat cgttttttgta gttacatatg     360 ggtttaaaac caatggaatc tacattgaac ttataacatt gtagctccaa agggcttgga     420
actctttgaa atggggagag aagtttaatc tggtgatggc tgtgactcgg gtaatcacat     480
cgtcatcggg tatatccgca gcggagctta aggttttgtt tctctttcgc taactcggtt     540
tcgctttaat tcaagaagat gataagataa gttgtaactt ttcggtttgt gtttgcattg     600
caacaggaac aagagaccga tgaaaacagt ggaagtttgc agctttacga acggctaagt     660
ttctcatacc cggcactcct aatgcctctt atacacgaaa gagataccgt aagcataaaa     720
accgaaacaa agcgacactc aaaaaaaccg tatgctgata agacttgacc aaataatgtg     780 ttttttttgcc ttgacagtat cttgcttggt cattgaagag aagtaaggca gtgaatgggt    840
gtaaaacagt ggtgggagtg atcgggaaag gacacatgaa tggtgtcatc tacgcgttgg     900
tgtcagactc tggggatctc cggtttagag atttggtggg aagaggagat tcatataatg     960
gtggtactgg tactacatcg aacggttgga ttcaaaaggt tttaaagagc ttcgtaagag    1020
acacaattat agggttcttg ctatgggagt tatatgaaca gtatctgatg atgaatcaaa    1080
acctttcatg atataactaa aaaaacaagt tgttgcatat ttaaaaagga aactggaaaa    1140
agaatctaaa tgagtacaat atgtatgtat atgattcttc ttcctctaga ttttgttgag    1200
gcaactacaa agtcttatat gaaattgatg tatattttgc agaaatttca attgtaaaca    1260
taaaatgttt aggtaaaaaa ttatttgtac ttctctagtt ggtaacgaaa taaaaataaa    1320
```

```
atatttttt   ttttaatata   tatatatata   tatataaa    tataaatata   tgtttaagat    1380
tcattatctg  gagagagagc   ctcgaagaaa   gcaaataaaa  tctagagaag   cttgtttcta    1440
gggtttcgac  tctcgacggc   cggtacgatt   tttcaactgc  ttgttctaag   gtataatcaa    1500
aatcgagttc  ttcagatatt   gaattcgatt   ctctctttgg  tctctctctt   ctcttgttct    1560
tcagatttaa  attcgatagc   ttttttcattt  tcttccgttg  aattttttctt  gtttcattag    1620 gtctgttgaa  attgtagttt   cttcttgctt   tgttttctca  tatggttgat   ttttttttc     1680 cagatctgag  gttttttttca  tcatagcttg   aaaaaatcca  tactttctgg   gcttcctttg    1740
tataaatatg  aaaactttaa   tgaaaatctg   ttgtggtatg  ttatgggttg   tgacttgtga    1800
tgaattgaat  tttgaatata   gttgtaaatt   tgaaatcttg  aagtatgaaa   tttgcattgg    1860
tttgttaatt  tgtgatgaat   tggattttga   ttattacagt  tataaagttg   aaaacttgga    1920
agtgtagatg  attacatttt   tctgtggttt   ggttcctgtt  atgttcattg   ttctatgatc    1980
ttaattatat  gttttgttat   tgcttctctt   ctggagtgtg  tttatttgta   tattttggtc    2040
aaatctgtgc  tctgtttagt   atctcttgga   tatcttttga  tacttaggtt   gttgagagga    2100
gctataaatc  gttctgttg    tctatttttgt  aggaatc                                2137

<210> SEQ ID NO 3
<211> LENGTH: 1408
<212> TYPE: DNA
<213> ORGANISM: Arabidopsis thaliana

<400> SEQUENCE: 3
aagcttttta   tttaccattg  ctcgcttttg   tacttcaacg  ttgatgaatg   tgtgtgtttg      60
ggatgatcat   aggagggcaa  actgcgttgg   cattgcgact  tctattggcg   gttttctctt    120
ctaagttatc   ttctgttgct  gaccgccctt   tcggggatga  ggtacttttg   agaaaacctc    180
aagagttagt   gtttgtcttt  ggacattcag   tctcttcttg  attgctattt   gttgcagttt    240
cgtgctgctc   ggaaagcatc  tgaggaagtt   ggtgcgcagc  tggttcttgg   agatcgaccc    300
atcgaaataa   ctgtaatgac  tataccaagt   accaactgat  cgttttttgta  gttacatatg    360 ggtttaaaac   caatggaatc  tacattgaac   ttataacatt  gtagctccaa   agggcttgga    420
actctttgaa   atggggagag  aagtttaatc   tggtgatggc  tgtgactcgg   gtaatcacat    480
cgtcatcggg   tatatccgca  gcggagctta   aggttttgtt  tctctttcgc   taactcggtt    540
tcgctttaat   tcaagaagat  gataagataa   gttgtaactt  ttcggtttgt   gtttgcattg    600
caacaggaac   aagagaccga  tgaaaacagt   ggaagtttgc  agctttacga   acggctaagt    660
ttctcatacc   cggcactcct  aatgcctctt   atacacgaaa  gagataccgt   aagcataaaa    720
accgaaacaa   agcgacactc  aaaaaaaccg   tatgctgata  agacttgacc   aaataatgtg    780 ttttttttgcc  ttgacagtat  cttgcttggt   cattgaagag  aagtaaggca   gtgaatgggt    840
gtaaaacagt   ggtgggagtg  atcgggaaag   gacacatgaa  tggtgtcatc   tacgcgttgg    900
tgtcagactc   tggggatctc  cggtttagag   atttggtggg  aagaggagat   tcatataatg    960
gtggtactgg   tactacatcg  aacggttgga   ttcaaaaggt  tttaaagagc   ttcgtaagag   1020
acacaattat   agggttcttg  ctatgggagt   tatatgaaca  gtatctgatg   atgaatcaaa   1080
acctttcatg   atataactaa  aaaaacaagt   tgttgcatat  ttaaaaagga   aactggaaaa   1140
agaatctaaa   tgagtacaat  atgtatgtat   atgattcttc  ttcctctaga   ttttgttgag   1200
gcaactacaa   agtcttatat  gaaattgatg   tatattttgc  agaaatttca   attgtaaaca   1260
taaaatgttt   aggtaaaaaa  ttatttgtac   ttctctagtt  ggtaacgaaa   taaaaataaa   1320
```

| | |
|---|---:|
| atatttttt tttaatata tatatatata tatatataaa tataaatata tgtttaagat | 1380 |
| tcattatctg gagagagagc ctcgaaga | 1408 |

<210> SEQ ID NO 4
<211> LENGTH: 1000
<212> TYPE: DNA
<213> ORGANISM: Arabidopsis thaliana

<400> SEQUENCE: 4

| | |
|---|---:|
| aaaagaatct aaatgagtac aatatgtatg tatatgattc ttcttcctct agattttgtt | 60 |
| gaggcaacta caaagtctta tatgaaattg atgtatattt tgcagaaatt tcaattgtaa | 120 |
| acataaaatg tttaggtaaa aaattatttg tacttctcta gttggtaacg aaataaaaat | 180 |
| aaaatatttt ttttttaat atatatatat atatatatat aaatataaat atatgtttaa | 240 |
| gattcattat ctggagagag agcctcgaag aaagcaaata aaatctagag aagcttgttt | 300 |
| ctagggtttc gactctcgac ggccggtacg attttcaac tgcttgttct aaggtataat | 360 |
| caaaatcgag ttcttcagat attgaattcg attctctctt tggtctctct cttctcttgt | 420 |
| tcttcagatt taaattcgat agcttttca ttttcttccg ttgaattttt cttgtttcat | 480 |
| taggtctgtt gaaattgtag tttcttcttg ctttgtttc tcatatggtt gatttttttt | 540 |
| ttccagatct gaggtttttt tcatcatagc ttgaaaaaat ccatactttc tgggcttcct | 600 |
| tgtataaat atgaaaactt taatgaaaat ctgttgtggt atgttatggg ttgtgacttg | 660 |
| tgatgaattg aattttgaat atagttgtaa atttgaaatc ttgaagtatg aaatttgcat | 720 |
| tggtttgtta atttgtgatg aattggattt tgattattac agttataaag ttgaaaactt | 780 |
| ggaagtgtag atgattacat ttttctgtgg tttggttcct gttatgttca ttgttctatg | 840 |
| atcttaatta tatgttttgt tattgcttct cttctggagt gtgtttattt gtatatttg | 900 |
| gtcaaatctg tgctctgttt agtatctctt ggatatcttt tgatacttag gttgttgaga | 960 |
| ggagctataa atcgtttctg ttgtctattt tgtaggaatc | 1000 |

<210> SEQ ID NO 5
<211> LENGTH: 729
<212> TYPE: DNA
<213> ORGANISM: Arabidopsis thaliana

<400> SEQUENCE: 5

| | |
|---|---:|
| aagcaaataa aatctagaga agcttgtttc tagggtttcg actctcgacg gccggtacga | 60 |
| ttttcaact gcttgttcta aggtataatc aaaatcgagt tcttcagata ttgaattcga | 120 |
| ttctctcttt ggtctctctc ttctcttgtt cttcagattt aaattcgata gcttttcat | 180 |
| ttcttccgt tgaattttc ttgttcatt aggtctgttg aaattgtagt ttcttcttgc | 240 |
| tttgttttct catatggttg attttttttt tccagatctg aggttttttt catcatagct | 300 |
| tgaaaaatc catactttct gggcttcctt tgtataaata tgaaaacttt aatgaaaatc | 360 |
| tgttgtggta tgttatgggt tgtgacttgt gatgaattga attttgaata tagttgtaaa | 420 |
| tttgaaatct tgaagtatga aatttgcatt ggtttgttaa tttgtgatga attggatttt | 480 |
| gattattaca gttataaagt tgaaaacttg gaagtgtaga tgattacatt tttctgtggt | 540 |
| ttggttcctg ttatgttcat tgttctatga tcttaattat atgttttgtt attgcttctc | 600 |
| ttctggagtg tgtttatttg tatattttgg tcaaatctgt gctctgttta gtatctcttg | 660 |
| gatatctttt gatacttagg ttgttgagag gagctataaa tcgtttctgt tgtctatttt | 720 |
| gtaggaatc | 729 |

```
<210> SEQ ID NO 6
<211> LENGTH: 26
<212> TYPE: DNA
<213> ORGANISM: Artificial Sequence
<220> FEATURE:
<223> OTHER INFORMATION: Description of Artificial Sequence: forward
      primer 1

<400> SEQUENCE: 6
aataagcttg aattagcatt gtgttg                                              26

<210> SEQ ID NO 7
<211> LENGTH: 27
<212> TYPE: DNA
<213> ORGANISM: Artificial Sequence
<220> FEATURE:
<223> OTHER INFORMATION: Description of Artificial Sequence: reverse
      primer 1

<400> SEQUENCE: 7
aatggatccg attcctacaa aatagac                                             27

<210> SEQ ID NO 8
<211> LENGTH: 29
<212> TYPE: DNA
<213> ORGANISM: Artificial Sequence
<220> FEATURE:
<223> OTHER INFORMATION: Description of Artificial Sequence: forward
      primer 2

<400> SEQUENCE: 8
aaatgtcgac aaagaatcta aatgagtac                                           29
```

ATRSP GENE PROMOTERS

RELATED APPLICATIONS

This application is a divisional of U.S. patent application Ser. No. 10/240,496, filed Oct. 2, 2002, now U.S. Pat. No. 7,256,276, which is a national phase of International Application No. PCT/EP01/03735, filed Apr. 2, 2001, both of which are herein incorporated by reference in their entirety.

The present invention relates to novel DNA sequences that function as promoters of transcription of associated nucleotide sequences in plants. More specifically, this invention relates to novel promoters that confer constitutive expression to an associated nucleotide sequence.

In the field of agriculture there exists a continuous desire to modify plants according to one's needs. One way to accomplish this is by using modern genetic engineering techniques. For example, by introducing a gene of interest into a plant, the plant can be specifically modified to express a desirable phenotypic trait. For this, plants are transformed most commonly with a heterologous gene comprising a promoter region, a coding region and a termination region. When genetically engineering a heterologous gene for expression in plants, the selection of a promoter is often a critical factor. While it may be desirable to express certain genes only in response to particular stimuli or confined to specific cells or tissues, other genes are more desirably expressed constitutively, i.e. throughout the plant at all times and in most tissues and organs. In the past, the 35S promoter from Cauliflower Mosaic Virus (CaMV 35S promoter) has been widely used for constitutive expression of heterologous genes in plants. There are, however, occasions where it is desirable to use alternative promoters. Therefore, it is a major objective of the present invention to provide such alternative promoters for expression of a nucleotide sequence of interest in plants. The invention also provides recombinant DNA molecules, expression vectors and transgenic plants comprising the promoters of the present invention.

The present invention thus provides:

a DNA sequence capable of driving expression of an associated nucleotide sequence, wherein said DNA sequence is obtainable from genes of the atRSp gene family. Preferred is a DNA sequence which is obtainable from atRSp41 and comprises the nucleotide sequence depicted in SEQ ID NO:1.
In particular, DNA sequences are provided, wherein
said DNA sequence comprises the nucleotide sequence depicted in SEQ ID NO:2
said DNA sequence comprises the nucleotide sequence depicted in SEQ ID NO:3
said DNA sequence comprises the nucleotide sequence depicted in SEQ ID NO:4
said DNA sequence comprises the nucleotide sequence depicted in SEQ ID NO:5

The invention further provides DNA sequences comprising a consecutive stretch of at least about 85 bases, preferably of between about 300 bases and about 500 bases, more preferably of between about 800 bases and about 1000 bases and most preferably of about 1500 bases in length of SEQ ID NO:1, wherein said DNA sequences are capable of driving expression of an associated nucleotide sequence.

In a particular embodiment of the invention said consecutive stretch of at least about 85 bases, preferably of between about 300 bases and about 500 bases, more preferably of between about 800 bases and about 1000 bases and most preferably of about 1500 bases in length has at least 75%, preferably 80%, more preferably 90% and most preferably 95% sequence identity with a corresponding consecutive stretch of at least about 85 bases, preferably of between about 300 bases and about 500 bases, more preferably of between about 800 bases and about 1000 bases and most preferably of about 1500 bases in length of SEQ ID NO:1.

The invention further provides recombinant DNA molecules comprising an atRSp41 promoter. In addition, the invention provides recombinant DNA molecules and DNA expression cassettes comprising a DNA sequence according to the invention operatively linked to a nucleotide sequence of interest, including vector molecules comprising said recombinant DNA and expression cassettes, respectively.

In particular, recombinant DNA molecules and DNA expression cassettes are provided wherein the nucleotide sequence of interest comprises a coding sequence and wherein
the coding sequence encodes a desirable phenotypic trait
the coding sequence encodes a selectable or screenable marker gene
the coding sequence encodes a protein conferring antibiotic resistance, virus resistance, insect resistance, disease resistance, or resistance to other pests, herbicide tolerance, improved nutritional value, improved performance in an industrial process or altered reproductive capability
the coding sequence encodes commercially valuable enzymes or metabolites in the plant
the coding sequence is in antisense orientation The invention further provides
host cells stably transformed with a DNA sequence, a recombinant DNA molecule or a DNA expression vector according to the invention. In particular, wherein
the host cell is a bacterium
the host cell is a plant cell
the host cell is a plant cell selected from the group consisting of rice, maize, wheat, barley, rye, sweet potato, sweet corn, bean, pea, chicory, lettuce, cabbage, cauliflower, broccoli, turnip, radish, spinach, asparagus, onion, garlic, pepper, celery, squash, pumpkin, hemp, zucchini, apple, pear, quince, melon, plum, cherry, peach, nectarine, apricot, strawberry, grape, raspberry, blackberry, pineapple, avocado, papaya, mango, banana, soybean, tomato, sorghum, sugarcane, sugar-beet, sunflower, rapeseed, clover, tobacco, carrot, cotton, alfalfa, potato, eggplant, cucumber, *Arabidopsis thaliana*, and woody plants such as coniferous and deciduous trees, but particularly rice, maize, wheat, barley, cabbage, cauliflower, pepper, squash, melon, soybean, tomato, sugar-beet, sunflower or cotton, rice, maize, wheat, *Sorghum bicolor*, orchardgrass, sugar beet and soybean cells
the host cell is a plant cell from a dicotyledonous plant
the host cell is a plant cell from a dicotyledonous plant selected from the group consisting of soybean, cotton, tobacco, sugar beet and oilseed rape
the host cell is a plant cell from a monocotyledonous plant
the host cell is a plant cell from a monocotyledonous plant selected from the group consisting of maize, wheat, sorghum, rye, oats, turf grass, rice, and barley.

In addition, plants and the progeny thereof including seeds are provided stably transformed with a DNA sequence, a recombinant DNA molecule or a DNA expression vector according to the invention. In particular, wherein
the plant is selected from the group consisting of rice, maize, wheat, barley, rye, sweet potato, sweet corn, bean, pea, chicory, lettuce, cabbage, cauliflower, broccoli, turnip, radish, spinach, asparagus, onion, garlic, pepper, celery, squash, pumpkin, hemp, zucchini, apple, pear, quince, melon, plum, cherry, peach, nectarine, apricot, strawberry, grape, raspberry, blackberry, pineapple, avocado, papaya, mango, banana, soybean, tomato, sorghum, sugarcane, sugar-beet, sunflower, rapeseed, clover, tobacco, carrot, cotton, alfalfa, potato, eggplant, cucumber, *Arabidopsis thaliana*, and woody plants such as coniferous and deciduous trees, but particularly rice, maize, wheat, barley, cabbage, cauliflower, pepper, squash, melon, soybean, tomato, sugar-beet, sunflower or cotton, rice, maize, wheat, *Sorghum bicolor*, orchardgrass, sugar beet and soybean.

The present invention further discloses the use of the DNA sequence according to the invention to express a nucleotide sequence of interest a method of producing a DNA sequence according to the invention, wherein the DNA is produced by a polymerase chain reaction wherein at least one oligonucleotide used comprises a sequence of nucleotides which represents a consecutive stretch of 15 or more base pairs of SEQ ID NO:1.

In order to ensure a clear and consistent understanding of the specification and the claims, the following definitions are provided:

atRSp: stands for *Arabidopsis thaliana* arginine/serine-type plant splicing factor.

DNA shuffling: DNA shuffling is a method to rapidly, easily and efficiently introduce rearrangements, preferably randomly, in a DNA molecule or to generate exchanges of DNA sequences between two or more DNA molecules, preferably randomly. The DNA molecule resulting from DNA shuffling is a shuffled DNA molecule that is a non-naturally occurring DNA molecule derived from at least one template DNA molecule.

Expression: refers to the transcription and/or translation of an endogenous gene or a transgene in plants. In the case of antisense constructs, for example, expression may refer to the transcription of the antisense DNA only.

Functionally equivalent sequence: refers to a DNA sequence which has promoter activity substantially similar to any of the atRSp promoters or parts thereof, but particularly to the atRSp41 promoter and which under stringent hybridizing conditions hybridizes with the said promoter sequences.

Gene: refers to a coding sequence and associated regulatory sequence wherein the coding sequence is transcribed into RNA such as mRNA, rRNA, tRNA, snRNA, sense RNA or antisense RNA. Examples of regulatory sequences are promoter sequences, 5'- and 3'-untranslated sequences and termination sequences. Further elements that may be present are, for example, introns.

Gene of interest: refers to any gene which, when transferred to a plant, confers upon the plant a desired characteristic such as antibiotic resistance, virus resistance, insect resistance, disease resistance, or resistance to other pests, herbicide tolerance, improved nutritional value, improved performance in an industrial process or altered reproductive capability. The "gene of interest" may also be one that is transferred to plants for the production of commercially valuable enzymes or metabolites in the plant.

Heterologous as used herein means of different natural or of synthetic origin. For example, if a host cell is transformed with a nucleic acid sequence that does not occur in the untransformed host cell, that nucleic acid sequence is said to be heterologous with respect to the host cell. The transforming nucleic acid may comprise a heterologous promoter, heterologous coding sequence, or heterologous termination sequence. Alternatively, the transforming nucleic acid may be completely heterologous or may comprise any possible combination of heterologous and endogenous nucleic acid sequences.

Marker gene: refers to a gene encoding a selectable or screenable trait.

Operatively linked to/associated with: a regulatory DNA sequence is said to be "operatively linked to" or "associated with" a DNA sequence that codes for an RNA or a protein if the two sequences are situated such that the regulatory DNA sequence affects expression of the coding DNA sequence.

Plant: refers to any plant, particularly to seed plants.

Plant cell: structural and physiological unit of the plant, comprising a protoplast and a cell wall. The plant cell may be in form of an isolated single cell or a cultured cell, or as a part of higher organized unit such as, for example, a plant tissue, or a plant organ.

Plant material: refers to leaves, stems, roots, flowers or flower parts, fruits, pollen, pollen tubes, ovules, embryo sacs, egg cells, zygotes, embryos, seeds, cuttings, cell or tissue cultures, or any other part or product of a plant.

Promoter: refers to a DNA sequence that initiates transcription of an associated DNA sequence. The promoter region may also include elements that act as regulators of gene expression such as activators, enhancers, and/or repressors and may include all or part of the 5'-untranslated region.

Recombinant DNA molecule: a combination of DNA sequences that are joined together using recombinant DNA technology.

Recombinant DNA technology: procedures used to join together DNA sequences as described, for example, in Sambrook et al., 1989, Cold Spring Harbor, N.Y.: Cold Spring Harbor Laboratory Press.

Screenable marker gene: refers to a gene whose expression does not confer a selective advantage to a transformed cell, but whose expression makes the transformed cell phenotypically distinct from untransformed cells.

Selectable marker gene: refers to a gene whose expression in a plant cell gives the cell a selective advantage. The selective advantage possessed by the cells transformed with the selectable marker gene may be due to their ability to grow in the presence of a negative selective agent, such as an antibiotic or a herbicide, compared to the growth of non-transformed cells. The selective advantage possessed by the transformed cells, compared to non-transformed cells, may also be due to their enhanced or novel capacity to utilize an added compound as a nutrient, growth factor or energy source. Selectable marker gene also refers to a gene or a combination of genes whose expression in a plant cell in the presence of the selective agent, compared to the absence of the selective agent, has a positive effect on the transformed plant cell and a negative effect on the untransformed plant cell, for example with respect to growth, and thus gives the transformed plant cell a positive selective advantage.

Sequence identity the percentage of sequence identity is determined using computer programs that are based on dynamic programming algorithms. Computer programs that are preferred within the scope of the present invention include the BLAST (Basic Local Alignment Search Tool) search programs designed to explore all of the available sequence databases regardless of whether the query is protein or DNA. Version BLAST 2.0 (Gapped BLAST) of this search tool has been made publicly available on the Internet (currently http://www.ncbi.nlm.nih.gov/BLAST/). It uses a heuristic algorithm, which seeks local as opposed to global alignments and is therefore able to detect relationships among sequences, which share only isolated regions. The scores assigned in a BLAST search have a well-defined statistical interpretation. Said programs are preferably run with optional parameters set to the default values.

Transformation: refers to the introduction of a nucleic acid into a cell. In particular, it refers to the stable integration of a DNA molecule into the genome of an organism of interest 5'-untranslated region: sequence in the DNA upstream of the coding region that is transcribed into RNA, but not translated into protein; corresponds to the region between the 5'-end of the RNA and the start codon.

The present invention relates to DNA sequences obtainable from genes of the atRSp gene family such as atRSp41. 'atRSp' stands for *Arabidopsis thaliana* arginine/serine-type plant splicing factor, and the two-digit number following 'atRSp' refers to the molecular mass of the putative protein encoded by the corresponding gene. Preferred is a DNA sequence which is obtainable from the atRSp41 gene of *Arabidopsis thaliana* which is capable of driving expression of an associated nucleotide sequence of interest. DNA sequences comprising functional and/or structural equivalents thereof are also embraced by the invention. The present invention thus relates to DNA sequences that function as promoters of transcription of associated nucleotide sequences. The promoter region may also include elements that act as regulators of gene expression such as activators, enhancers, and/or repressors and may include the 5'-untranslated region.

In a preferred embodiment of the invention, said DNA sequence confers constitutive expression to an associated nucleotide sequence. Constitutive expression means that the nucleotide sequence of interest is expressed at all times and in most tissues and organs. When tested in association with a GUS reporter gene in transgenic *Arabidopsis thaliana*, the DNA sequence according to the invention confers expression of the GUS reporter gene in all or most of the following organs and tissues: leaves, roots, flowers, flower buds, veins, trichomes, hydathodes, sepals, anthers, filaments, pollen, stigma, style, root meristem, root elongation zone, root specialization zone and lateral root primordium. When tested in 3-day-old transgenic *Arabidopsis thaliana* seedlings, expression of the GUS reporter gene is predominantly detected in the cotyledons, in the roots and in the root and shoot meristems. Quantitative analysis of GUS expression in *Arabidopsis* plants shows that the promoters of the invention confer a high level constitutive expression to the GUS reporter gene. Thus, the DNA sequence according to the invention is useful for high level expression of an associated nucleotide sequence of interest, which preferably is a coding sequence. It is known to the skilled artisan that the associated coding sequence of interest can be expressed in sense or in antisense orientation. Further, the coding sequence of interest may be of heterologous or homologous origin with respect to the plant to be transformed. In case of a homologous coding sequence, the DNA sequence according to the invention is useful for ectopic expression of said sequence. In one particular embodiment of the invention expression of the coding sequence of interest under control of a DNA sequence according to the invention suppresses its own expression and that of the original copy of the gene by a process called cosuppression.

One preferred embodiment of the invention is the DNA sequence depicted in SEQ ID NO:1, called the atRSp41 (2327) promoter. SEQ ID NO:1 is identical to a region of the sequenced *Arabidopsis thaliana* chromosome 5, P1 clone: MSG15 (GenBank accession number AB015478). The inventors are the first to demonstrate that SEQ ID NO:1 has promoter activity and belongs to the atRSp41 gene. The atRSp41(2327) promoter contains 1598 bp of 5'-upstream sequence and 729 bp of 5'-untranslated sequence of the atRSp41 gene. This DNA sequence is obtainable by PCR with genomic DNA from *Arabidopsis thaliana* using forward primer 1 (SEQ ID NO:6) with a HindIII restriction site and reverse primer 1 (SEQ ID NO:7) containing a BamHI restriction site. The putative TATA box of the atRSp41(2327) promoter is located at bases 1551 to 1556 of SEQ ID NO:1, and the start of transcription is at base 1599 of SEQ ID NO:1. The region extending from base 1599 through 2327 is the so-called 5'-untranslated region (5'-UTR) of the atRSp41 gene which is transcribed but not translated into protein. It is known to the skilled artisan that 5'-untranslated regions can contain regulatory elements with important functions in gene expression. The 5'-UTR of the atRSp41 gene contains a long intron extending from base 1681 through 2322 of SEQ ID NO:1.

The DNA sequences of the invention can be obtained, for example, by PCR with genomic DNA from *Arabidopsis thaliana* or from any other plant species comprising homologues of the DNA sequence of the invention using sequence specific primers. It is apparent to the skilled artisan that, based on the sequence shown in SEQ ID NO:1, any primer combination of interest can be chosen to PCR amplify shorter DNA that can be used according to the invention. The invention thus includes shorter fragments derived from the atRSp41 promoter that function according to the invention i.e. are capable of conferring expression of an associated nucleotide sequence. This can be tested by making deletions in the promoter and then assaying for retention of promoter activity. Such assays are within the skill of the ordinary artisan. Shorter DNA fragments are of at least about 85 bases, preferably of between about 300 bases and about 500 bases, more preferably of between about 800 bases and about 1000 bases and most preferably of about 1500 bases in length. Another preferred embodiment of the invention is the DNA sequence depicted in SEQ ID NO:2, called the atRSp41(2137) promoter. This DNA sequence contains 1408 bp of 5'-upstream sequence and 729 bp of 5'-untranslated sequence of the atRSp41 gene. This 2137 bp long DNA fragment can be obtained, for example, by partial restriction of the DNA sequence obtained by PCR amplification of genomic DNA with forward primer 1 and reverse primer 1 (see above) with the restriction endonucleases HindIII and BamHI. The 2327 bp PCR fragment obtained by amplification with forward primer 1 and reverse primer 1 contains 2 internal HindIII restriction sites, one at base 191 and the other one at base 1618 of SEQ ID NO:1. The first one, at base 191 of SEQ ID NO:1, is used for cloning, the second one at base 1618 of SEQ ID NO:1 remains intact during partial restriction with HindIII. The resulting 2137 bp HindIII/BamHI atRSp41 fragment (SEQ ID NO:2) then can be used according to the invention.

A further preferred embodiment of the invention is the atRSp41(1408) promoter, the sequence of which is depicted in SEQ ID NO:3: The atRSp41(1408) promoter contains 1408 bp of 5'-upstream sequence of the atRSp41 gene.

Yet another preferred embodiment of the invention is the atRSp41(1000) promoter depicted in SEQ ID NO:4. This DNA sequence is obtainable by PCR with genomic DNA from *Arabidopsis thaliana* using forward primer 2 (SEQ ID NO:8) with a SalI restriction site and reverse primer 1 (SEQ ID NO:7) containing a BamHI restriction site. The atRSp41 (1000) promoter consists of 271 bp of 5'-upstream sequence and 729 bp of 5'-untranslated sequence (5'-UTR) of the atRSp41 gene.

Another preferred embodiment of the invention is the sequence depicted in SEQ ID NO:5 containing 729 bp of 5'-untranslated sequence (5'-UTR) of the atRSp41 gene. The 5'-UTR contains a 642 bp intron located at base 83 to base 724 of SEQ ID NO:5. This DNA fragment can be used in combination with homologous or heterologous promoter fragments to regulate expression of an associated nucleotide sequence.

It is clear to the skilled artisan that mutations, insertions, deletions and/or substitutions of one or more nucleotides can be introduced into the DNA sequence of SEQ ID NO:1 or shorter fragments thereof, including the fragments provided in SEQ ID NO:2, SEQ ID NO:3, SEQ ID NO:4 or SEQ ID NO:5, using methods known in the art. In addition, an unmodified or modified nucleotide sequence of the present invention can be varied by shuffling the sequence of the invention. To test for a function of variant DNA sequences according to the invention, the sequence of interest is operably linked to a selectable or screenable marker gene and expression of the reporter gene is tested in transient expression assays with protoplasts or in stably transformed plants. It is known to the skilled artisan that DNA sequences capable of driving expression of an associated nucleotide sequence are build in a modular way. Accordingly, expression levels from shorter DNA fragments may be different than the one from the longest fragment and may be different from each other. For example, deletion of a down-regulating upstream element will lead to an increase in the expression levels of the associated nucleotide sequence while deletion of an up-regulating element will decrease the expression levels of the associated nucleotide sequence. It is also known to the skilled artisan that deletion of development-specific or a tissue-specific element will lead to a temporally or spatially altered expression profile of the associated nucleotide sequence. Embraced by the present invention are also functional equivalents of the promoters of the present invention, i.e. nucleotide sequences that hybridize under stringent conditions to any one of SEQ ID NO:1, SEQ ID NO:2, SEQ ID NO:3, SEQ ID NO:4 or SEQ ID NO:5. A stringent hybridization is performed at a temperature of 65° C., preferably 60° C. and most preferably 55° C. in double strength (2×) citrate buffered saline (SSC) containing 0.1% SDS followed by rinsing of the support at the same temperature but with a buffer having a reduced SSC concentration. Such reduced concentration buffers are typically one tenth strength SSC (0.1×SSC) containing 0.1% SDS, preferably 0.2×SSC containing 0.1% SSC and most preferably half strength SSC (0.5×SSC) containing 0.1% SDS. In fact, functional equivalents of the atRSp41 promoters from other organisms can be found by hybridizing any one of SEQ ID NO:1, SEQ ID NO:2, SEQ ID NO:3, SEQ ID NO:4 or SEQ ID NO:5 with genomic DNA isolated from an organism of interest. The skilled artisan knows how to proceed to find such sequences as there are many ways known in the art to identify homologous sequences in other organisms. Such newly identified DNA molecules then can be sequenced and the sequence can be compared to any one of SEQ ID NO:1, SEQ ID NO:2, SEQ ID NO:3, SEQ ID NO:4 or SEQ ID NO:5 and tested for promoter activity. Within the scope of the present invention are DNA molecules having at least 75%, preferably 80%, more preferably 90%, and most preferably 95% sequence identity to the nucleotide sequence of any one of SEQ ID Nos:1, 2, 3, 4 or 5. The percentage of sequence identity is determined using computer programs that are based on dynamic programming algorithms. Computer programs that are preferred within the scope of the present invention include the BLAST (Basic Local Alignment Search Tool) search programs designed to explore all of the available sequence databases regardless of whether the query is protein or DNA. Version BLAST 2.0 (Gapped BLAST) of this search tool has been made publicly available on the Internet (currently http://www.ncbi.nlm.nih.gov/BLAST/). It uses a heuristic algorithm which seeks local as opposed to global alignments and is therefore able to detect relationships among sequences which share only isolated regions. The scores assigned in a BLAST search have a well-defined statistical interpretation. Said programs are preferably run with optional parameters set to the default values.

It is another object of the present invention to provide recombinant DNA molecules comprising a DNA sequence according to the invention operably linked to a nucleotide sequence of interest. The nucleotide sequence of interest can, for example, code for a ribosomal RNA, an antisense RNA or any other type of RNA that is not translated into protein. In another preferred embodiment of the invention the nucleotide sequence of interest is translated into a protein product. The nucleotide sequence associated with the promoter sequence may be of homologous or heterologous origin with respect to the plant to be transformed. The sequence may also be entirely or partially synthetic. Regardless of the origin, the associated DNA sequence will be expressed in the transformed plant in accordance with the expression properties of the promoter to which it is linked. In case of homologous nucleotide sequences associated with the promoter sequence, the promoter according to the invention is useful for ectopic expression of said homologous sequences. Ectopic expression means that the nucleotide sequence associated with the promoter sequence is expressed in tissues and organs and/or at times where said sequence may not be expressed under control of its own promoter. In one particular embodiment of the invention, expression of nucleotide sequence associated with the promoter sequence suppresses its own expression and that of the original copy of the gene by a process called cosuppression.

In a preferred embodiment of the invention, the associated nucleotide sequence may code for a protein that is desired to be expressed throughout the plant at all times and in most tissues and organs. Such nucleotide sequences preferably encode proteins conferring a desirable phenotypic trait to the plant transformed therewith. Examples are nucleotide sequences encoding proteins conferring antibiotic resistance, virus resistance, insect resistance, disease resistance, or resistance to other pests, herbicide tolerance, improved nutritional value, improved performance in an industrial process or altered reproductive capability. The associated nucleotide sequence may also be one that is transferred to plants for the production of commercially valuable enzymes or metabolites in the plant. Embraced by the present invention are also selectable or screenable marker genes, i.e. genes comprising a DNA sequence of the invention operably linked to a coding region encoding a selectable or screenable trait.

Examples of selectable or screenable marker genes are described below. For certain target species, different antibiotic or herbicide selection markers may be preferred. Selection markers used routinely in transformation include the nptII gene which confers resistance to kanamycin, paromomycin, geneticin and related antibiotics (Vieira and Messing, 1982, Gene 19: 259-268; Bevan et al., 1983, Nature 304:184-187) the bacterial aadA gene (Goldschmidt-Clermont, 1991, Nucl. Acids Res. 19: 4083-4089), encoding aminoglycoside 3'-adenylyltransferase and conferring resistance to streptomycin or spectinomycin, the hph gene which confers resistance to the antibiotic hygromycin (Blochlinger and Diggelmann, 1984, Mol. Cell. Biol. 4: 2929-2931), and the dhfr gene, which confers resistance to methotrexate (Bourouis and Jarry, 1983, EMBO J. 2: 1099-1104). Other markers to be used include a phosphinothricin acetyltransferase gene, which confers resistance to the herbicide phosphinothricin (White et al., 1990, Nucl. Acids Res. 18: 1062; Spencer et al. 1990, Theor. Appl. Genet. 79: 625-631), a mutant EPSP synthase gene encoding glyphosate resistance (Hinchee et al., 1988, Bio/Technology 6: 915-922), a mutant acetolactate synthase (ALS) gene which confers imidazolione or sulfonylurea resistance (Lee et al., 1988, EMBO J. 7: 1241-1248), a mutant psbA gene conferring resistance to atrazine (Smeda et al., 1993, Plant Physiol. 103: 911-917), or a mutant protoporphyrinogen oxidase gene as described in EP 0769 059. Selection markers resulting in positive selection, such as a phosphomannose isomerase gene, as described in patent application WO 93/05163, are also used. Identification of transformed cells may also be accomplished through expression of screenable marker genes such as genes coding for chloramphenicol acetyl transferase (CAT), β-glucuronidase (GUS), luciferase (LUC), and green fluorescent protein (GFP) or any other protein that confers a phenotypically distinct trait to the transformed cell. It is a further objective of the invention to provide recombinant expression vectors comprising a DNA sequence of the invention fused to an associated nucleotide sequence of interest. In these vectors, foreign DNA can be inserted into a polylinker region such that these exogenous sequences can be expressed in a suited host cell which may be, for example, of bacterial or plant origin. For example, the plasmid pBI101 derived from the *Agrobacterium tumefaciens* binary vector pBIN19 allows cloning and testing of promoters using β-glucuronidase (GUS) expression signal (Jefferson et al, 1987, EMBO J. 6: 3901-3907). The size of the vector is 12.2 kb. It has a low-copy RK2 origin of replication and confers kanamycine resistance in both bacteria and plants. There are numerous other expression vectors known to the person skilled in the art that can be used according to the invention. It is a further objective of the present invention to provide transgenic plants comprising the recombinant DNA sequences of the invention. The invention thus relates to plant cells, to plants derived from such cells, to plant material, to the progeny and to seeds derived from such plants, and to agricultural products with improved properties obtained by any one of the transformation methods described below. Plants transformed in accordance with the present invention may be monocots or dicots and include, but are not limited to, rice, maize, wheat, barley, rye, sweet potato, sweet corn, bean, pea, chicory, lettuce, cabbage, cauliflower, broccoli, turnip, radish, spinach, asparagus, onion, garlic, pepper, celery, squash, pumpkin, hemp, zucchini, apple, pear, quince, melon, plum, cherry, peach, nectarine, apricot, strawberry, grape, raspberry, blackberry, pineapple, avocado, papaya, mango, banana, soybean, tomato, sorghum, sugarcane, sugarbeet, sunflower, rapeseed, clover, tobacco, carrot, cotton, alfalfa, potato, eggplant, cucumber, *Arabidopsis thaliana*, and woody plants such as coniferous and deciduous trees. Preferred plants to be transformed are rice, maize, wheat, barley, cabbage, cauliflower, pepper, squash, melon, soybean, tomato, sugar-beet, sunflower or cotton, but especially rice, maize, wheat, *Sorghum bicolor*, orchardgrass, sugar beet or soybean. The recombinant DNA sequences of the invention can be introduced into the plant cell by a number of well-known methods. Those skilled in the art will appreciate that the choice of such method might depend on the type of plant which is targeted for transformation, i.e., monocot or dicot. Suitable methods of transforming plant cells include microinjection (Crossway et al., 1986, Bio Techniques 4:320-334), electroporation (Riggs and Bates, 1986, Proc. Natl. Acad. Sci., USA 83:5602-5606), *Agrobacterium*-mediated transformation (Hinchee et al., 1988, Bio/Technology 6:915-922; EP 0 853 675), direct gene transfer (Paszkowski et al., 1984, EMBO J. 3:2717-2722), and ballistic particle acceleration using devices available from Agracetus, Inc., Madison, Wis. and Dupont, Inc., Wilmington, Del. (see, for example, U.S. Pat. No. 4,945,050 and McCabe et al., 1988, Bio/Technology 6:923-926). The cells to be transformed may be differentiated leaf cells, embryogenic cells, or any other type of cell.

In the direct transformation of protoplasts, the uptake of exogenous genetic material into a protoplast may be enhanced by the use of a chemical agent or an electric field. The exogenous material may then be integrated into the nuclear genome. The previous work is conducted in dicot tobacco plants, which resulted in the foreign DNA being incorporated and transferred to progeny plants (Paszkowski et al., 1984, EMBO J. 3:2712-2722; Potrykus et al., 1985, Mol. Gen. Genet. 199:169-177). Monocot protoplasts, for example, of *Triticum* monococcum, *Lolium multiflorum* (Italian rye grass), maize, and Black Mexican sweet corn, are transformed by this procedure. An additional preferred embodiment is the protoplast transformation method for maize as disclosed in EP 0 292 435, as well as in EP 0 846 771. For maize transformation also see Koziel et al., 1993, Bio/Technology 11:194-200. Transformation of rice can be carried out by direct gene transfer techniques utilizing protoplasts or particle bombardment. Protoplast-mediated transformation is described for Japonica-types and Indica-types (Zhang et al., 1988, Plant Cell Rep., 7:379-384; Shimamoto et al., 1989, Nature 338:274-276; Datta et al., 1990, Bio/Technology 8:736-740). Above both types are also routinely transformable using the particle bombardment (Christou et al., 1991, Bio/Technology 9:957-962). Patent application No. EP 0 332 581 describes techniques for the generation, transformation and regeneration of Pooideae protoplasts. These techniques allow the transformation of all Pooideae plants including *Dactylis* and wheat. Furthermore, wheat transformation is described in patent application No. EP 0 674 715; and by Weeks et al., 1993 (Plant Physiol. 102:1077-1084).

The thus-constructed plant expression vector can, for example, be introduced into the calli of rice according to the conventional plant transformation method, and the differentiation of roots and leaves is induced therefrom, and then, can be transferred to a flowerpot for cultivation, thereby obtaining the transformed rice.

The plants resulting from transformation with the DNA sequences or vectors of the present invention will express a nucleotide sequence of interest throughout the plant and in most tissues and organs.

The genetic properties engineered into the transgenic plants described above are passed on by sexual reproduction or vegetative growth and can thus be maintained and propagated in progeny plants. Generally said maintenance and propagation make use of known agricultural methods developed to fit specific purposes such as tilling, sowing or harvesting. Specialized processes such as hydroponics or greenhouse technologies can also be applied. Use of the advantageous genetic properties of the transgenic plants according to the invention can further be made in plant breeding that aims at the development of plants with improved properties such as tolerance of pests, herbicides, or stress, improved nutritional value, increased yield, or improved structure causing less loss from lodging or shattering. The various breeding steps are characterized by well-defined human intervention such as selecting the lines to be crossed, directing pollination of the parental lines, or selecting appropriate progeny plants. Depending on the desired properties different breeding measures are taken. The relevant techniques are well known in the art and include but are not limited to hybridization, inbreeding, backcross breeding, multiline breeding, variety blend, interspecific hybridization, aneuploid techniques, etc. Hybridization techniques also include the sterilization of plants to yield male or female sterile plants by mechanical, chemical or biochemical means. Cross pollination of a male sterile plant with pollen of a different line assures that the genome of the male sterile but female fertile plant will uniformly obtain properties of both parental lines. Thus, the transgenic plants according to the invention can be used for the breeding of improved plant lines that for example increase the effectiveness of conventional methods such as herbicide or pesticide treatment or allow to dispense with said methods due to their modified genetic properties. Alternatively new crops with improved stress tolerance can be obtained that, due to their optimized genetic "equipment", yield harvested product of better quality than products that were not able to tolerate comparable adverse developmental conditions.

It is another objective of the present invention to provide DNA sequences that can be used to express a nucleotide of interest in a desired organism. This organism can be a bacterium, a plant or any other organism of interest.

Furthermore, the disclosure of SEQ ID NO:1 enables a person skilled in the art to design oligonucleotides for polymerase chain reactions which attempt to amplify DNA fragments from templates comprising a sequence of nucleotides characterized by any continuous sequence of 15 and preferably 20 to 30 or more base pairs in SEQ ID NO:1. Said nucleotides comprise a sequence of nucleotides which represents 15 and preferably 20 to 30 or more base pairs of SEQ ID NO:1. Polymerase chain reactions performed using at least one such oligonucleotide and their amplification products constitute another embodiment of the present invention.

BRIEF DESCRIPTION OF THE SEQUENCES IN THE SEQUENCE LISTING

SEQ ID NO:1 atRSp41(2327) promoter
SEQ ID NO:2 atRSp41(2137) promoter
SEQ ID NO:3 atRSp41(1408) promoter
SEQ ID NO:4 atRSp41(1000) promoter
SEQ ID NO:5 atRSp41 5'-UTR
SEQ ID NO:6 forward primer 1
SEQ ID NO:7 reverse primer 1
SEQ ID NO:8 forward primer 2

EXAMPLES

Standard recombinant DNA and molecular cloning techniques used here are well known in the art and are described, for example, by Sambrook et al., 1989, "Molecular Cloning", Cold Spring Harbor, Cold Spring Harbor Laboratory Press, NY and by Ausubel et al., 1994, "Current protocols in molecular biology", John Wiley and Sons, New York.

Example 1

Construction of atRSp41 Promoters

Genomic DNA from *Arabidopsis thaliana* is isolated from green parts of 3-week-old *Arabidopsis* plants according to the method of Soni and Murray (1994) Analytical Biochemistry 218, 474-476. A 2327 bp long fragment (SEQ ID NO:1) of the atRSp41 promoter is obtained by PCR with genomic DNA from *Arabidopsis thaliana* using forward primer 1 (5'-aatAAGCTTgaattagcattgtgttg-3', SEQ ID NO:6) with a HindIII restriction site and reverse primer 1 (5'-aatGGATCCgattcctacaaaatagac-3', SEQ ID NO:7) containing a BamHI restriction site. The restriction sites are indicated in capital letters. The fragment is amplified in 100 μl reaction volume containing 100 μM of each forward and reverse primer, 62 μM of each dNTP, 10 μl of Taq polymerase reaction buffer (Gibco), 500 ng of total genomic DNA from *Arabidopsis*, and 2 units of Taq polymerase (Gibco) using the following thermal program: 1× (95° C., 2 min); 36× (95° C. for 30 sec., 55° C. for 60 sec., 72° C. for 60 sec.) and 1×(72° C. for 5 min).

The 2327 bp PCR fragment contains 2 internal HindIII restriction sites, one at base 191 and the other one at base 1618 of SEQ ID NO:1. The first one, at base 191 of SEQ ID NO:1, is used for cloning, the second one at base 1618 of SEQ ID NO:1 remains intact during partial restriction with HindIII. The resulting 2137 bp HindIII/BamHI atRSp41 fragment (SEQ ID NO:2) is ligated into the HindIII/BamHI polylinker cloning site of the vector pBI101 (Clontech) so that the ligated fragment can drive the β-glucuronidase (GUS) coding sequence linked to the NOS 3'-termination signal (Jefferson et al, 1987, EMBO J. 6: 3901-3907). The resulting plasmid is called p41I. The promoter-reporter gene construct comprised in p41I is called atRSp41(2137)-GUS. The nucleotide sequence of the cloned DNA fragment is determined by DNA sequencing using standard procedures known in the art.

The 2137 bp HindIII/BamHI atRSp41 fragment contains 1408 bp of 5'-upstream sequence (SEQ ID NO:3) and 729 bp of 5'-untranslated sequence (SEQ ID NO:5). The 5'-untranslated sequence contains a 642 bp intron from base 1681 to base 2322 of SEQ ID NO:1.

The parent plasmid pBI101 is derived from the *Agrobacterium tumefaciens* binary vector pBIN19 and allows cloning and testing of promoters using β-glucuronidase (GUS) expression. The size of the vector is 12.2 kb. It has a low-copy RK2 origin of replication and confers kanamycine resistance in both bacteria and plants.

The atRSp41(1000) promoter (SEQ ID NO:4) is obtained by PCR with genomic DNA from *Arabidopsis thaliana* using forward primer 2 (5'-aaatGTCGACaaagaatctaaatgagtac-3', SEQ ID NO:8) containing a SalI restriction site and reverse primer 1 (5'-aatGGATCCgattcctacaaaatagac-3', SEQ ID NO:7) with a BamHI restriction site. The restriction sites are indicated in capital letters. The fragment is amplified in 100 μl reaction volume containing 100 μM of each forward and reverse primer, 62 μM of each dNTP, 10 μl of Taq polymerase reaction buffer (Gibco), 500 ng of total genomic DNA from *Arabidopsis*, and 2 units of Taq polymerase (Gibco) using the following thermal program: 1× (95° C., 2 min); 36× (95° C. for 30 sec., 55° C. for 60 sec., 72° C. for 60 sec.) and 1× (72° C. for 5 min). The resulting PCR fragment is cut with SalI and BamHI and ligated into the SalI/BamHI polylinker cloning site of the vector pBI101 (Clontech) so that the ligated fragment can drive the n-glucuronidase (GUS) coding sequence, which is linked to the NOS 3'-termination signal (Jefferson et al., 1987, EMBO J, 6: 3901-3907). The promoter-reporter gene construct comprised in this plasmid is termed atRSp (1000)-GUS. The nucleotide sequence of the cloned DNA fragment is determined by standard DNA sequencing techniques.

Example 2

Preparation of Solutions and Media for Plant Regeneration and Transformation

Culture media GM, CIM and SIM are the media described by Valvekens et al. (1988, Proc. Natl. Acad. Sci. USA. 85: 5536-5540).

Culture medium GM contains the mineral salts of Murashige and Skoog (1962, Physiol. Plant. 15:473-497), 1.0 mg/l thiamine (stock 1 mg/ml), 0.5 mg/l pyridoxine HCl (stock 1 mg/ml), 0.5 mg/l nicotinic acid (stock 1 mg/ml), 0.5 g/l 2-(N-morpholino)ethanesulfonic acid (MES), 10 g/l sucrose, 8 g/l agar, with the pH adjusted to 5.8 with 1N KOH. CIM contains the mineral salts and vitamins of B5 medium (Gamborg et al., 1968, Exp. Cell Res. 50:151-158), 0.5 g/l 2-(N-morpholino) ethanesulfonic acid (MES), 20 g/l glucose, 0.5 mg/l 2,4-dichlorophenoxyacetic acid (2,4-D) (stock 10 mg/ml in DMSO), 0.05 mg/l kinetin (stock 5 mg/ml in DMSO), pH 5.8. Solid CIM medium contains 8 g/l agar. SIM contains the mineral salts and vitamins of B5 medium (Gamborg et al., 1968, supra), 0.5 g/l 2-(N-morpholino)ethanesulfonic acid (MES), 20 g/l glucose, 5 mg/l N-6-(2-isopentenyl)adenine (2iP) (stock 20 mg/ml in DMSO), 0.15 mg/l indole-3-acetic-acid (IAA) (stock 1.5 mg/ml in DMSO), 8 g/l agar, pH 5.8. SIM V750 K100 is SIM medium supplemented with 750 mg/l vancomycin and 100 mg/l kanamycin. SIM V500 K100 is SIM medium supplemented with 500 mg/l vancomycin and 100 mg/l kanamycin. GM K50 is GM medium supplemented with 50 mg/l kanamycin.

The culture media are all sterilized by autoclaving (20 min, 121° C.). Vitamins are dissolved in water and added to media before autoclaving. Hormones are dissolved in dimethyl sulfoxide (DMSO). Antibiotics are dissolved in water and sterilized by filtration (0.22 μm). Hormones and antibiotics are added after autoclaving and cooling of the media to 65° C. In all cases 9-cm Petri dishes (Falcon, 3003) are used, except for GM and GM K50 which are usually poured into 15-cm Petri dishes (Falcon, 3025).

Plates with solid media are dried before usage in laminar flow to remove condensate.

Example 3

Arabidopsis Strain and Growth Conditions

Arabidopsis thaliana seeds ecotype Columbia (Col-0) wild type are purchased from Lehle Seeds, USA (1102 South Industrial Blvd. Suite D, Round Rock Tex. 78681, USA). Plants are grown at 22° C. 16/8 hour light/dark cycle in pots in the mixture of 4 parts sand, 4 parts garden soil and 1 part agrilit.

Example 4

Agrobacterium Strain and Culture

Vector plasmids are introduced into recipient Agrobacterium tumefaciens strain LBA4404 (Clontech) by triparental mating according to the protocol described by Walkerpeach and Velten ("Agrobacterium-mediated gene transfer to plant cells: Cointegrate and binary vector systems". in: Plant Molecular Biology Manual, B1: 1-19, 1994. Eds.: S. B. Gelvin, R. A., Schilperoort, Kluvers Acad. Publishers). Mobilizing strain used is E. coli HB101 harboring conjugation plasmid pRK2013 (Ditta et al., 1980, Broad host range DNA cloning system from Gram-negative bacteria. Construction of gene bank of Rhizobium meliloti. Proc. Natl. Acad. Sci. USA 77: 7347-7351). Agrobacteria used for root transformation are grown in LB medium (Sambrook et al., 1989, "Molecular Cloning", Cold Spring Harbor, Cold Spring Harbor Laboratory Press, NY) without antibiotics at 28° C. and 200 rpm.

Example 5

Seed Sterilization

Seeds are placed in 70% EtOH/0.05% Tween 20 for 1 minute in a 2 ml Eppendorf tube. 70% EtOH/0.05% Tween 20 is removed with a pipette and replaced with 5% NaOCl/0.05% Tween 20 for 15 minutes. Seeds are shaken regularly; The solution is removed in sterile conditions and the seeds are washed in sterile, distilled water 3 times for 10 minutes each. After the last wash seeds are keep in 0.5-1 ml water. Seeds can be used immediately or stored at 4° C. for two-three weeks. Sterilized seeds (20-30) are transferred with forceps on GM medium in 15-cm Petri dishes. Seedlings are grown in vertically placed plates in a growth chamber (22° C.; 16/8 hour light/dark cycle).

Example 6

Transformation of Root Explants of Arabidopsis thaliana

Roots of three-week-old seedlings are used in the transformation procedure. Roots should not be green or brown. Green parts of seedlings are removed with scalpel and forceps. Remaining roots are collected and approximately 5 entire root systems are placed per plate with solid CIM medium. Roots are pressed gently onto the surface of the plate to ensure full contact with the medium, but they should not be dipped into the agar. Roots are incubated for three days in a growth chamber (22° C.; 16/8 hour light/dark cycle). Roots are then transferred to a sterile Petri dish with filter paper wetted with liquid CIM medium and cut with a scalpel in 0.5-1 cm pieces. Root explants are then transferred to a 50 ml sterile Falcon tube containing 10 ml of liquid CIM medium. To this, 0.5 ml of an overnight Agrobacterium culture (OD 0.6-1) is added and incubate for 1-2 minutes while shaking gently. The liquid is poured out of the tube through sterile metal screens (50 mesh, Sigma, S-0895), which are kept with forceps. Roots usually remain on the wall of the tube close to its edge. Then the root explants are transferred to a sterile Petri dish with filter paper and briefly blotted dry to remove excess of liquid. Root explants are put onto plates with solid CIM medium and incubated in a growth chamber for 2 days under dim light (1.5-2 klux). Slight traces of overgrowth with Agrobacterium should be visible after the period of cocultivation. Root explants are then transferred to sterile 50 ml Falcon tubes with 20 ml of liquid CIM medium, supplemented with 1000 mg/l vancomycin. The Falcon tubes are then gently vortexed to remove the Agrobacteria. The liquid is poured out of the tube as described above and the explants are briefly blotted dry on filter paper. Explants are then transferred to plates containing SIM V750 K100 medium. Roots should be in a close contact with the medium. The explants are incubated in a growth chamber in normal conditions for one week and then transferred to SIM V500 K100 medium and incubated for an additional week. Then the amount of vancomycin is reduced to 250 mg/l. First shoots should appear at the end of the third week of cultivation on SIM media. Shoots are excised when 0.3-0.5-cm long, any residual callus is removed, and the shoots are transferred to 15-cm plates containing GM K50 medium. Max. 3 shoots are placed per plate. To get more shoots, the remaining root explants can be transferred to fresh SIM plates supplemented with 125 mg/l vancomycin and 100 mg/l kanamycin for additional two weeks. Rooted shoots can be transferred to soil to allow seed set. Shoots that do not root are transferred to Magenta jars (one per jar) containing GM medium to produce seeds in vitro.

Seeds from individual transgenic plants are germinated on GM K50 medium in growth chamber for 2 weeks. Phenotypically normal kanamycin resistant seedlings, which form green true leaves and branched root system, are selected for further analyses.

Example 7

Histochemical β-Glucuronidase (GUS) Assay

In vitro grown seedlings or plants grown in soil are used in GUS assays. Either whole seedlings or dissected organs are dipped into GUS staining solution. GUS staining solution contains 1 mM 5-bromo-4-chloro-3-indolyl glucuronide (X-Gluc, Duchefa, 20 mM stock in DMSO), 100 mM Na-phosphate buffer pH 7.0, 10 mM EDTA pH 8.0, and 0.1% Triton ×100. Tissue samples are incubated at 37° C. for 1-16 hours. If necessary samples can be cleared with several washes of 70% EtOH to remove chlorophyll.

Results of the histochemical GUS assay are shown in Table 1:

TABLE 1

Histochemical GUS assay in *Arabidopsis* plants transformed with construct atRSp41(2137)-GUS

|  |  | atRSp41(2137)-GUS |
|---|---|---|
| leaf |  | + |
|  | veins | + |
|  | trichomes | + |
|  | hydathodes | + |
| stem |  | (+) |
|  | trichomes | (+) |
| opened flowers |  | + |
|  | sepal | + |
|  | petal | − |
|  | anther | + |
|  | filament | + |
|  | pollen | + |
|  | stigma | + |
|  | style | + |
|  | ovules | ND |
| flower buds |  | + |
|  | sepal | + |
|  | petal | − |
|  | anther | − |
|  | microspore | − |
|  | stigma | + |
|  | style | + |
| root |  | + |
|  | root meristem | + |
|  | elongation zone | + |
|  | specialization zone | + |
|  | lateral root primordium | + |
| 1-day-old seedling |  | + |
|  | cotyledons | + |
|  | hypocotyl | + |
|  | root | + |
|  | root meristem | + |
| 3-day-old seedling |  | + |
|  | cotyledons | + |
|  | shoot meristem | + |
|  | hypocotyl | − |
|  | root | + |
|  | root meristem | + |

+ tissue stained
(+) tissue stained after wounding
ND—not determined

Except for petals, anthers and microspores, GUS activity is found in all organs and tissues tested. These results indicate that atRSp41 promoter is a DNA sequence conferring constitutive expression to the GUS reporter gene.

Example 8

Fluorimetric GUS Assay

Fluorimetric GUS assay is done according to Jefferson et al., 1987 (EMBO J. 6: 3901-3907). Tissue samples are frozen in liquid nitrogen and either stored at −80° C. until required or used immediately. Tissue sample (100 mg) is ground in (200 µl) extraction buffer. Debris is pelleted by centrifugation (14000 rpm, 15 min, 4° C.). Clear supernatant is assayed for total protein using the Bio-Rad kit according to the manufacturers' recommendations. An aliquot of supernatant containing 20 mg total protein is dissolved in an equal volume of extraction buffer. Prewarmed to 37° C. extraction buffer containing 2 mM 4-methyl-umbelliferyl-β-D-glucuronide (MUG) is added to a final volume of 200 µl. The mixture is vortexed briefly and incubated at 37° C. for a fixed time in the range of 10 to 30 minutes. The reaction is stopped by the addition of 0.8 ml 0.2 M $Na_2CO_3$. Fluorescence at 455 nm is measured using a Hitachi Fluorescence Spectrophotometer F-4500 at an excitation of 365 nm.

Measurement of GUS-activity in extracts of 10-day-old *Arabidopsis* seedlings transformed with atRSp41(2137)-GUS, atRSp41(1000)-GUS or, for comparison, 35S-CaMV-GUS shows that the atRSp41 promoter is a very active promoter, even if the shorter promoter, atRSp41(1000) is used. The results are shown in Table 2.

TABLE 2

Fluorimetric GUS assay with extracts of *Arabidopsis* plants transformed with different promoter constructs

| | GUS-activity (nmol 4-methylumbellifery glucuronide $min^{-1}$ mg $protein^{-1}$) | | |
|---|---|---|---|
| Promoter | CaMV 35S-GUS | atRSp41 (2137)-GUS | atRSp41 (1000)-GUS |
| Experiment 1 | 1440 | 10680 | 5470 |
| Experiment 2 | 1670 | 9320 | 8030 |
| Experiment 3 |  | 3999 |  |
| average | 1555 | 8000 | 6750 |

The CaMV 35S-GUS construct is from plasmid pBI121 (Jefferson et al, 1987, EMBO J. 6, 3091-3907).

Example 9

Transient Expression Experiments

1. Suspension Cultures and Protoplast Preparation

*Orychophragmus violates*. Suspension cultures are maintained in 40 ml of MS medium (Murashige and Skoog, Physiol Plant 15, 474-497, 1962) including 100 mg/ml inositol, 2% sucrose, and 0.1 mg/ml 2.4 D. Protoplasts are isolated from 4- to 5-day-old-cultures. Cell walls are digested at 26° C. for 1 hr in 0.1% pectolyase Y23 (Seishin Pharmaceutical Co., Japan), 1% cellulase Onozuka R10 (Yakult Honsha Co., Japan), 0.4 M D-mannitol, and 0.1% MES, pH 5.5. Protoplasts are filtered through a 50 µm sieve and washed twice with electroporation (EP) solution (10 mM HEPES, 150 mM NaCl, 5 mM $CaCl_2$, 0.2 M mannitol, pH 7.1).

*Nicotiana plumbaginifolia*. Plants are maintained axenically on RPM2 medium (Blonstein et al. Mol Gen Genet. 211, 252-259, 1988) plus 7 g/l bacto agar, pH 5.6. For protoplast preparation, leaves are cut and incubated overnight at 26° C. in a solution of 0.5% driselase (Fluka), 0.25 mM PVP 10 (polyvinylpyrrolydon MW 10000), 3.85 mM $CaCl_2$, 6 mg/l NAA, 2 mg/l BAP, and 0.5 M sucrose, pH 5.7. Protoplasts are filtered through a 100 μm sieve. Sucrose solution (0.6 M sucrose, 0.1% MES, and 15 mM $CaCl_2$, pH 5.7) is added to the protoplast suspension for the first purification step, and the suspension is overlayed with W5 solution (150 mM NaCl, 125 mM $CaCl_2$, 5 mM KCl, 6 mM glucose; Menczel et al., Theor Appl Genet. 59, 191-195, 1981). Protoplasts are then washed once with W5 solution and finally with EP solution.

2. Transient Expression Experiment Transfection by Electroporation of $2\times10^6$

*Orychophragmus violaceus* protoplasts in 0.66 ml EP buffer is carried out by discharging a 960 μF capacitor through a distance of 4 mm of protoplast suspension. The capacitor is loaded at the 450 Volts. Electroporation is performed in the presence of 5-10 μg of plasmid DNA to be tested for reporter gene expression, then protoplasts are cultivated 16 to 24 hours at 25° C. Transfection of $2\times10^6$ *Nicotiana plumbaginifolia* protoplasts in 0.3 ml suspension is carried out in the presence of 0.3 ml PEG (40% polyethyleneglycole 6000) and 5-10 μg of plasmid DNA. Protoplast are cultivated in 0.4 ml K3 medium (Godall et al., Methods Enzymol 181, 148-161, 1990) for 16 to 24 hours at 25° C. and added with 10 ml W5 buffer before harvesting.

Protein extracts are prepared by at least three cycles of freezing and thawing, and clarified by centrifugation.

What is claimed is:

1. A transgenic plant cell comprising a recombinant polynucleotide comprising a promoter operably linked to a heterologous nucleotide sequence of interest, wherein said promoter drives expression of said heterologous nucleotide sequence of interest, and wherein said promoter comprises a DNA sequence selected from the group consisting of SEQ ID NO:1, SEQ ID NO:2, SEQ ID NO:3, SEQ ID NO:4, and SEQ ID NO:5.

2. The transgenic plant cell of claim 1 wherein the transgenic plant cell is a monocot cell or a dicot cell.

3. A transgenic plant comprising a recombinant polynucleotide, and any progeny of said plant, comprising a promoter operably linked to a heterologous nucleotide sequence of interest, wherein said promoter drives expression of said heterologous nucleotide sequence of interest, and wherein said promoter comprises a DNA sequence selected from the group consisting of SEQ ID NO:1, SEQ ID NO:2, SEQ ID NO:3, SEQ ID NO:4, and SEQ ID NO:5, and wherein said progeny comprise said recombinant polynucleotide.

4. The transgenic plant of claim 3 wherein the plant is selected from the group consisting of maize, wheat, sorghum, rye, oats, turf grass, barley, soybean, cotton, tobacco, sugar beet and oilseed rape.

* * * * *